United States Patent [19]

Mayhew et al.

[11] Patent Number: 6,007,839

[45] Date of Patent: *Dec. 28, 1999

[54] PREPARATION OF PHARMACEUTICAL COMPOSITIONS CONTAINING ETHERLIPID-CONTAINING MULTIPLE LIPID LIPOSOMES

[75] Inventors: Eric Mayhew, Monmouth Junction, N.J.; Andrew S. Janoff, Yardley, Pa.; Imran Ahmad, Plainsboro, N.J.; Suresh K. Bhatia, New Delhi, India

[73] Assignee: The Liposome Company, Inc., Princeton, N.J.

[ * ] Notice: This patent is subject to a terminal disclaimer.

[21] Appl. No.: 09/017,439

[22] Filed: Feb. 2, 1998

Related U.S. Application Data

[63] Continuation-in-part of application No. 08/602,669, Feb. 16, 1996, Pat. No. 5,762,958.

[51] Int. Cl.$^6$ .................................................. A61K 9/127

[52] U.S. Cl. ............................ 424/450; 264/4.1; 264/4.3; 428/402.2

[58] Field of Search .................................... 424/450, 1.21, 424/9.321, 9.51; 264/4.1, 4.3; 428/402.2

[56] References Cited

U.S. PATENT DOCUMENTS

| | | | |
|---|---|---|---|
| 3,752,886 | 8/1973 | Munder et al. | 424/199 |
| 4,159,988 | 7/1979 | Eibl et al. | 260/340.9 |
| 4,163,748 | 8/1979 | Eibl et al. | 260/403 |
| 4,382,035 | 5/1983 | Eibl | 260/403 |
| 4,734,225 | 3/1988 | Eibl | 260/386 |
| 4,804,789 | 2/1989 | Eibl | 568/853 |
| 4,920,016 | 4/1990 | Allen et al. | 424/450 |
| 4,965,391 | 10/1990 | Counsell et al. | 558/169 |
| 4,983,397 | 1/1991 | Schroit | 424/450 |
| 5,013,556 | 5/1991 | Woodle | 424/450 |
| 5,436,234 | 7/1995 | Eibl | 514/77 |
| 5,762,958 | 6/1998 | Mayhew | 424/450 |

FOREIGN PATENT DOCUMENTS

| | | | |
|---|---|---|---|
| 4132345 | 4/1993 | Germany | A61K 31/685 |
| 4408011 | 11/1995 | Germany | A61K 31/685 |
| 072294 | 7/1984 | Japan . | |
| 1583661 | 1/1981 | United Kingdom | A61K 31/66 |
| 93/04673 | 3/1993 | WIPO | A61K 9/127 |
| 93/08202 | 4/1993 | WIPO | C07H 15/04 |
| 94/27580 | 12/1994 | WIPO | A61K 9/127 |

OTHER PUBLICATIONS

Bazill, et al., "Role of Endocytosis in the Action of Ether Lipids on WEHI–3B, HL60, and FEDCP–Mix A4 Cells", Cancer Res. 50: 7505 (1990).

Berdel, "Membrane–interactive lipids as experimental anticancer drugs", Br. J. Cancer 64: 208 (1991).

Berdel, "Ether Lipids and Derivatives as Investigational Anticancer Drugs", Onkologie 13: 245 (1990).

Bhatia, et al., "Sterospecific Synthesis of Antitumor Active Thioether PAF Analogs", Lipids 26(12): 1424 (1991).

(List continued on next page.)

*Primary Examiner*—Gollamudi S. Kishore
*Attorney, Agent, or Firm*—Rosanne Goodman

[57] ABSTRACT

Described herein are methods of preparing liposome-containing pharmaceutical compositions, the liposomes containing headgroup-derivatized lipids and etherlipids having the formula:

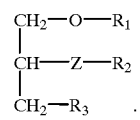

Such compositions are useful in the treatment of a variety of conditions, including various cancers and inflammatory disorders.

10 Claims, 3 Drawing Sheets

OTHER PUBLICATIONS

Blume et al, "Specific targeting with poly(ethylene glycol)–modified liposomes: coupling of homing devices to the ends of the polymeric chains combines effective target binding with long circulation times" Biochim. Biophys. Acta. 1149: 180–184 (1993).

Daicho, et al., "Effects of alkyl glycosides incorporated into liposomes prepared from synthetic amphiphiles on their tissue distribution in Ehrlich solid tumor–bearing mice", BBA, 1107:61 (1992).

Darnell et al., *Molecular Cell Biology,* Scientific American Books, Inc. (1986), New York, pp. 573–575.

Deamer and Uster, "Liposome Preparation: Methods and Mechanisms," in: *Liposomes* (M. Ostro, ed.), Marcel Dekker, Inc., New York (1983), pp. 27–52.

Dietzfelbinger et al., "Removal of Breast Cancer Cells from Bone Marrow by in Vitro Purging with Ether Lipids and Cryopreservation", Cancer Res. 53: 3747 (1993).

Dive, et al., "Multiparametric Flow Cytometry of the Modulation of Tumore Cell Membrane Permeability by Developmental Antitumore Ether Lipid SRI 62–834 in EMT6 Mouse Mammary Tumor and HL–60 Human Promyelocytic Leukemia Cells", Cancer Res., 51:799 (1991).

Gabizon et al., "Prolongation of Circulation Time of Doxorubicin Encapsulated in Liposomes Containing a Polyethylene Glycol–Derivatized Phospholipid: Pharmacokinetic Studies in Rodents and Dogs", Pharm. Res. 10(5): 703 (1993).

Kaufmann–Kolle, et al., "Liposomal Hexadecylphosphocholine (HEPC): in Vitro and in Vivo Application", Chemical Abs. V4, 10.08.

Layton et al., "The Interaction of Liposomes with Cells: The Relation of Cell Specific Toxicity to Lipid Composition", Eur. J. Cancer 16: 64 (1980).

Lewis and McElhaney, "The Mesomorphic Phase Behavior of Lipid Bilayers," in *The Structure of Biological Membranes* (P. Yeagle, ed.), CRC Press, Inc. (1992), Boca Raton, Fl., pp. 73–155, at pp. 123–126.

Muschiol et al., "Alkyl Phosphocholine: Toxicity and Anti-cancer Properties", Lipids 22(11): 930 (1987).

Nairn, in: *Remington's Pharmaceutical Science* (A. Gennaro, ed.), Mack Publishing Co., Easton, PA, (1985), pp. 1492–1517.

Park et al., "Some negatively charged phopholipid derivatives prolong the liposome circulation in vivo", Biochim. Biophys. Acta. 1108: 257 (1992).

Powis et al., "Selective Inhibition of Phophatidylinositol Phospholipase C by Cytotoxic Ether Lipid Analogues", Cancer Res. 52: 2835 (1992).

Powis et al., "The Cell Membrane and Cell Signals as Targets in Cancer Chemotherapy", Cancer Res. 50: 2203 (1990).

Reed et al., "Antineoplastic Ether–linked Phopholipid induces differentiation of acute myelogenous leukemic KG–1 cells into marcophase–like cells", Life Sci. 49: 1221 (1991).

Runge et al., "Destruction of Human Solid Tumors by Alkyl Lysophopholipids", JNCI. 64(6): 1301 (1980).

Tritton, et al., "How to Kill Cancer Cells: Membranes and Cell Signaling as Targets in Cancer Chemotherapy", Cancer Cells 2(4): 95 (1990).

Workman, "Antitumor Ether Lipids: Endocytosis as a Determinant of Cellular Sensitivity", Cancer Cells 3(8): 315 (1991).

Workman et al., "Plastelet–activating factor (PAF) antagonist WEB 2086 does not modulate the cytotoxicity of PAF or antitumor alkyl lysophospholipids ET–18–O–Methyl and SRIU 62–834 in HL–60 promyelocytic leukaemic cells", Biochem. Pharmacol. 41(2): 319 (1991).

Zeisig etal., "Antineoplastic activity in vitro of free and liposomal alkylphophocholines", Anti–Cancer Drugs 4: 57 (1993).

Kuchera AIDS Res. & Human Retroviruses 6 #4 p. 491, 1990.

Baker Int. J. Immuno Pharm. 13 #4, p. 385, 1991.

PREPARATION OF PHARMACEUTICAL COMPOSITIONS CONTAINING ETHERLIPID-CONTAINING MULTIPLE LIPID LIPOSOMES

This application is a CIP of 08/602,669 filed Feb. 16, 1996 now U.S. Pat. No. 5,762,958.

Etherlipids are synthetic analogues of platelet activating factor (PAF; 1-O-alkyl-2-acetyl-sn-glycero-3-phosphocholine), an effector generally believed to be involved in a variety of physiological processes, such as inflammation, the immune response, allergic reactions and reproduction. Etherlipids have been shown to be effective antitumor agents in animals, and are believed to be selectively cytotoxic to a broad variety of cancer cells (see, for example, Dietzfelbinger et al. (1993); Zeisig et al. (1993); Powis et al. (1990); Berdel (1991); Bhatia and Hadju (1991); Reed et al. (1991); Workman (1991); Workman et al. (1991); Bazill and Dexter (1990); Berdel (1990); Counsell et al. (1990); Tritton and Hickman (1990); Muschiol et al. (1990); Layton et al. (1980); Runge et al. (1980); Great Britain Patent No. 1,583,661; U.S. Pat. No. 3,752,886). Etherlipids have also been shown to be antimetastatic and anti-invasive, and to be capable of cell differentiation induction.

Mechanisms of etherlipid cytotoxicity, while not definitively established, appear to involve action at, and possible disruption of, the cell membrane. The selective cytotoxicity of etherlipids may involve intracellular accumulation and differential activity of alkyl cleavage enzymes. Etherlipids may also be selective inhibitors of phosphatidylinositol phospholipase C and protein kinase C activities, as well as of phosphatidylcholine biosynthesis. Hence, etherlipids are potentially quite useful as therapeutic agents. However, their administration can also lead to hemolysis, hepatic dysfunction and gastrointestinal disorders. Applicants have found that certain liposomal formulations of etherlipids can buffer these toxicities without inhibiting anticancer efficacy, and thereby can provide a more therapeutically useful basis for etherlipid administration.

SUMMARY OF THE INVENTION

This invention provides a method of preparing a pharmaceutical composition, the method comprising the steps of: preparing a liposome having a bilayer which has a lipid component comprising a phosphatidylethanolamine-based headgroup-derivatized lipid and an etherlipid of the formula and, combining the liposome with a pharmaceutically acceptable carrier. Such compositions are useful in the treatment of disorders susceptible to treatment with etherlipids, e.g., cancers and inflammatory conditions.

BRIEF DESCRIPTION OF THE DRAWINGS

FIG. 1. Time Course of Carboxyfluorescein Leakage from Liposomal Edelfosine Formulations Incubated at 48 deg. Celsius in PBS. ELL 28 (uppermost curve, "ELL" indicating "etherlipid liposome"): Distearoyl phosphatidylcholine ("DSPC"); cholesterol ("CHOL"); dioleoyl phosphatidylethanolamine-glutaric acid ("DOPE-GA"); edelfosine "EL," standing for "etherlipid" (the respective molar ratio of these lipid components being 4:3:1:2); ELL 30 (second from top curve): EPC:CHOL:DOPE-GA:EL (4:3:1:2); ELL 25 (middle curve): DOPE:CHOL:DOPE-GA:EL (3:3:1:3); ELL 12 (second from bottom curve): DOPC:CHOL:DOPE-GA:EL (4:3:1:2); and, ELL 20 (bottom curve): DOPE:CHOL:DOPE-GA:EL (4:3:1:2). Y-axis: % CF Leakage; x-axis: time (seconds).

DETAILED DESCRIPTION OF THE INVENTION

This invention provides methods of preparing liposome-containing pharmaceutical compositions; the liposome's bilayers have lipid components comprising headgroup-derivatized lipids and etherlipids.

"Liposomes" are self-assembling structures comprising one or more lipid bilayers, each of which surrounds an aqueous compartment and comprises two opposing monolayers of amphipathic lipid molecules. Amphipathic lipids comprise a polar (hydrophilic) headgroup region covalently linked to one or two non-polar (hydrophobic) acyl chains. Energetically unfavorable contacts between the hydrophobic acyl chains and the aqueous medium are generally believed to induce lipid molecules to rearrange such that the polar headgroups are oriented towards the aqueous medium while the acyl chains reorient towards the interior of the bilayer. An energetically stable structure is formed in which the acyl chains are effectively shielded from coming into contact with the aqueous medium.

Liposomes can have a single lipid bilayer (unilamellar liposomes, "ULVs"), or multiple lipid bilayers (multilamellar liposomes, "MLVs"), and can be made by a variety of methods (for a review, see, for example, Deamer and Uster (1983)). These methods include without limitation: Bangham's methods for making multilamellar liposomes (MLVs); Lenk's, Fountain's and Cullis' methods for making MLVs with substantially equal interlamellar solute distribution (see, for example, U.S. Pat. Nos. 4,522,803, 4,588,578, 5,030,453, 5,169,637 and 4,975,282); and Papahadjopoulos et al.'s reverse-phase evaporation method (U.S. Pat. No. 4,235,871) for preparing oligolamellar liposomes. ULVs can be produced from MLVs by such methods as sonication (see Papahadjopoulos et al. (1968)) or extrusion (U.S. Pat. No. 5,008,050 and U.S. Pat. No. 5,059,421). The etherlipid liposome of this invention can be produced by the methods of any of these disclosures, the contents of which are incorporated herein by reference.

Various methodologies, such as sonication, homogenization, French Press application and milling can be used to prepare liposomes of a smaller size from larger liposomes. Extrusion (see U.S. Pat. No. 5,008,050) can be used to size reduce liposomes, that is to produce liposomes having a predetermined mean size by forcing the liposomes, under pressure, through filter pores of a defined, selected size. Tangential flow filtration (see WO89/008846), can also be used to regularize the size of liposomes, that is, to produce liposomes having a population of liposomes having less size heterogeneity, and a more homogeneous, defined size distribution. The contents of these documents are incorporated herein by reference. Liposome sizes can also be determined by a number of techniques, such as quasi-electric light scattering, and with equipment, e.g., Nicomp® particle sizers, well within the possession of ordinarily skilled artisans. The contents of these disclosures are incorporated herein by reference.

Liposome preparation herein preferably involves the steps of: dissolving the lipid components of the liposome in an organic solvent, generally accomplished by addition of the lipids to a solvent-containing vessel, with swirling of the vessel's contents; removing organic solvent from the resulting lipid solution, generally accomplished by sparging the solution under an inert gas; and, hydrating the resulting dried lipid with an aqueous phase, so as to form liposomes.

Preferably, the liposomes used in this invention are unilamellar; accordingly, liposomes resulting from the preparation process described hereinabove are preferably subjected to extrusion, so as to reduce their lamellarity and increase their size homogeneity. The liposomes are most preferably between 50 and 200 nm in diameter; such smaller liposomes are generally believed to circulate longer in mammals, which are more quickly recognized by the mammals' reticuloendothelial systems ("RES"). Longer circulation can enhance therapeutic efficacy by allowing more liposomes to reach their intended site of actions, e.g., tumors or inflammations. However, small unilamellar liposomes, i.e., those generally less than 50 nm in diameter, carry amounts of bioactive agents which may be, in some cases, too low to be of sufficient therapeutic benefit. Accordingly, filters giving rise to 50–200 nm liposomes following extrusion, e.g., polycarbonate or aluminum oxide filters having pores whose average diameter is about 100 nm, are preferred for use herein.

Liposomes can be loaded with one or more biologically active agents by solubilizing the agent in the lipid or aqueous phase used to prepare the liposomes. Additionally or alternatively, ionizable bioactive agents can be loaded into liposomes by first forming the liposomes, establishing an electrochemical potential, e.g., by way of a pH gradient, across the outermost liposomal bilayer, and then adding the ionizable agent to the aqueous medium external to the liposome (see Bally et al. U.S. Pat. No. 5,077,056 and WO86/01102, the contents of which are incorporated herein by reference).

A "headgroup-derivatized" lipid is a lipid which, when present in a liposomal lipid bilayer with an etherlipid, can buffer the toxicity of the etherlipid. That is, the derivatized lipid can decrease the etherlipid's toxicity, such that it is generally less toxic than the free form of the etherlipid. Headgroup-derivatized lipids generally are amphipathic lipids comprising hydrophobic acyl chains, and a polar group to which a suitable chemical moiety has been attached.

Acyl chains are those which can adopt compatible packing configurations with the hydrophobic portions of other lipids present in the bilayer, and which can interact with an etherlipid such that release of the etherlipid from the bilayer is inhibited and etherlipid toxicity is buffered; such chains typically are saturated or unsaturated and contain from 4 to 24 carbon atoms in a straight chain, more preferably, 16–18 carbons. The polar group is typically a phosphorylethanolamine group.

Preferably, the headgroup derivatized lipid used herein is dipalmitoyl phosphatidylethanolamine ("DPPE"), palmitoyloleoyl phosphatidylethanolamine ("POPE") or dioleoyl phosphatidylethanolamine ("DOPE"). Most preferably, presently, the lipid is DOPE. Chemical moieties suitable for attachment to such lipids are those, such as dicarboxylic acids, gangliosides, polyethylene glycols, polyalkyl ethers and the like, which can be attached to the amino group of a phosphorylethanolamine, and which give rise to lipids having toxicity buffering properties. Means of identifying suitable chemical moieties, for example by subjecting derivatized lipids to in vitro and in vivo toxicity testing, are well known to, and readily practiced by, ordinarily skilled artisans given the teachings of this invention. Means of attaching chemical moieties to phosphorylethanolamine groups are also well known to, and readily practiced by, ordinarily skilled artisans.

The toxicity buffering capacities of headgroup-derivatized lipids can also be determined by a number of in vitro and in vivo testing methods well known to, and readily practiced by, ordinarily skilled artisans, given the teachings of this invention. For example, etherlipid-induced red blood cell (RBC) hemolysis can be examined in vitro by combining an etherlipid with an RBC suspension, incubating the combination, and then quantitating the percentage of RBC lysis.

Toxicity-buffering can further be assessed by determining the etherlipid's therapeutic window "TW," which is a numerical value derived from the relationship between the compound's induction of hemolysis and its ability to inhibit the growth of tumor cells. TW values are determined in accordance with the formula $HI5/Gl_{50}$ (wherein "$HI_5$" equals the concentration of compound inducing the hemolysis of 5% of the red blood cells in a culture, and wherein "$Gl_{50}$" equals the dose of compound inducing fifty percent growth inhibition in a population of cells exposed to the agent). The higher an agent's $HI_5$ value, the less hemolytic is the agent—higher $HI_5$'s mean that greater concentrations of compound are required to be present in order for the compound to induce 5% hemolysis. Hence, the higher its $HI_5$, the more therapeutically beneficial is a compound, because more of it can be given before inducing the same amount of hemolysis as an agent with a lower $HI_5$. By contrast, lower $Gl_{50}$'s indicate better therapeutic agents—a lower $Gl_{50}$ value indicates that a lesser concentration of an agent is required for 50% growth inhibition. Accordingly, the higher is its $HI_5$ value and the lower is its $Gl_{50}$ value, the better are a compound's agent's therapeutic properties.

Generally, when a bioactive agent's TW is less than 1, it cannot be used effectively as a therapeutic agent. That is, the agent's $HI_5$ value is sufficiently low, and its $Gl_{50}$ value sufficiently high, that it is generally not possible to administer enough of the agent to achieve a sufficient level of tumor growth inhibition without also attaining an unacceptable level of hemolysis. Etherlipid liposomes having bilayers that also comprise headgroup-derivatized lipids have TW's of greater than 1. Preferably, the TW of an etherlipid in a liposomal bilayer also comprising a headgroup-derivatized lipid is greater than about 1.5, more preferably, greater than about 2, and still more preferably, greater than about 3.

Headgroup-derivatized lipids can also be circulation-enhancing lipids, that is, the modifications directed to lipid toxicity buffering can also afford circulation enhancement. Accordingly, headgroup-derivatized lipids can inhibit clearance of liposomes from the circulatory systems of animals to which they have been administered. Liposomes are generally believed to be cleared from an animal's body by way of its reticuloendothelial system (RES). Avoiding RES clearance means that the frequency of liposome administration can be reduced, and that less of a liposome-associated bioactive agent need be administered to achieve desired serum levels of the agent. Enhanced circulation times can also allow targeting of liposomes to non-RES containing tissues.

Liposome outer surfaces are believed to become coated with serum proteins, such as opsonins, in animals' circulatory systems. Without intending in any way to be limited by theory, it is believed that liposome clearance can be inhibited by modifying the outer surface of liposomes such that binding of serum proteins thereto is generally inhibited. Effective surface modification, that is, alterations to the outer surfaces of liposomes which result in inhibition of opsonization and RES uptake, is believed to be accomplished by incorporating into liposomal bilayers lipids whose polar headgroups have been derivatized by attachment thereto of a chemical moiety which can inhibit the binding of serum proteins to liposomes such that the pharmacokinetic behavior of the liposomes in the circulatory systems of animals is altered (see, e.g., Blume et al. (1993); Gabizon et al. (1993); Park et al. (1992); Woodle et al. U.S. Pat. No. 5,013,556; and, U.S. Pat. No. 4,837,028).

The headgroup-derivatized comprises from about 5 mole percent to about 20 mole percent of the liposome's bilayer.

The etherlipid has the formula:

and,

$R_1$ of the etherlipid, the chain attached at the carbon #1 position of its glycerol backbone by way of an oxygen, has the formula $Y_1Y_2$. $Y_2$ is $CH_3$ or $CO_2H$, but preferably is $CH_3$. $Y_1$ can be branched or unbranched, but preferably, is a straight-chained moiety having the formula $—(CH_2)_{n1}(CH=CH)_{n2}(CH_2)_{n3}(CH=CH)_{n4}(CH_2)_{n5}(CH=CH)_{n6}(CH_2)_{n7}(CH=CH)_{n8}(CH_2)_{n9}$; the sum of n1+2n2+n3+2n4+n5+2n6+n7+2n8+n9 is an integer of from 3 to 23; that is, the acyl chain is from 4–24 carbon atoms in length. n1 is equal to zero or is an integer of from 1 to 23; n3 is equal to zero or is an integer of from 1 to 20; n5 is equal to zero or is an integer of from 1 to 17; n7 is equal to zero or is an integer of from 1 to 14; n9 is equal to zero or is an integer of from 1 to 11; and each of n2, n4, n6 and 8 is independently equal to zero or 1.

The hydrocarbon chain is preferably saturated, that is, it preferably has no double bonds between adjacent carbon atoms, each of n2, n4, n6 and n8 then being equal to zero. Accordingly, $Y_1$ is preferably $(CH_2)_{n1}$. More preferably, $R_1$ is $(CH_2)_{n1}CH_3$, and most preferably, is $(CH_2)_{17}CH3$. Alternatively, the chain can have one or more double bonds, that is, it can be unsaturated, and one or more of n2, n4, n6 and n8 can be equal to 1. For example, when the unsaturated hydrocarbon has one double bond, n2 is equal to 1, n4, n6 and n8 are each equal to zero and $Y_1$ is $(CH_2)_{n1}CH=CH(CH_2)_{n3}$. n1 is then equal to zero or is an integer of from 1 to 21, and n3 is also zero or is an integer of from 1 to 20, at least one of n1 or n3 not being equal to zero.

Z is oxygen, sulfur, NH, or —NHC(O)—, Z then being connected to the methyl group by way of either the nitrogen or carbonyl carbon. Z can also be —OC(O)—, it then being connected to the methyl group by way of either the oxygen or carbonyl carbon atom. Preferably, Z is O; accordingly, this invention's glycerol-based etherlipids preferably have a methoxy group at the sn-2 position of their glycerol backbone.

$R_2$ is an alkyl group, or a halogen-substituted alkyl group, having the formula $(C(X_1)_{n10}(X_2)_{n11})_{n12}CX_3X_4X_5$, wherein each of $X_1$, $X_2$, $X_3$, $X_4$, and $X_5$ is independently hydrogen or a halogen, but is preferably hydrogen. n10 is equal to zero, 1 or 2; n11 is equal to zero, 1, or 2; and n12 is equal to zero or an integer of from 1 to 23, but is most preferably, zero, $R_2$ then being $CX_3X_4X_5$. $X_3$, $X_4$, and $X_5$ are most preferably H, $R_2$ then being $CH_3$. Accordingly, the etherlipid preferably has a methyl group attached to its carbon #2. However, $R_2$ can then also be $CH_2F$, $CHF_2$ or $CF_3$. When n12 is not zero, the sum of n10+n11 is equal to 2, n12 is preferably equal to 1, and $R_2$ is preferably $CH_2CH_3$, $CH_2CF_3$ or $CF_2CF_3$.

Most preferably, the etherlipid is one in which $Y_2$ is $CH_3$, $R_1$ is $(CH_2)_{n1}CH_3$, $R_2$ is $CH_3$ and Z is O. The preferred etherlipid is therefore:

that is, 1-O-octadecyl-2-O-methyl-sn-glycero-3-phosphocholine ("ET-18-OCH$_3$" or "edelfosine").

The liposome's lipid bilayer can also contain a sterol, which generally affects the fluidity of lipid bilayers (see, for example, Lewis and McElhaney (1992) and Darnell et al. (1986)) Accordingly, sterol interactions with surrounding hydrocarbon chains generally inhibit emigration of these chains from the bilayer. The sterol of the liposomes of this invention is preferably, but not necessarily, cholesterol, and can also be a variety of other sterolic compounds. The bilayer can further comprise a phosphatidylcholine ("PC"); preferably, such a PC has two acyl chains, at least one of which has at least one double bond between adjacent carbon atoms. More preferably, presently, the PC is dioleoyl phosphatidylcholine ("DOPC").

The liposomes of this invention can comprise one or more additional lipids as well, that is, lipids in addition to the headgroup-derivatized lipid, etherlipid, and, optionally, phosphatidylcholine and sterol, already present in the liposomes' bilayers. Additional lipids are selected for their ability to adapt compatible packing conformations with the other lipid components of the bilayer such that the lipid constituents are tightly packed, and release of the lipids from the bilayer is inhibited. Lipid-based factors contributing to compatible packing conformations are well known to ordinarily skilled artisans and include, without limitation, acyl chain length and degree of unsaturation, as well as the headgroup size and charge. Accordingly, suitable additional lipids, including various phosphatidylethanolamines ("PE's") such as egg phosphatidylethanolamine ("EPE") or dioleoyl phosphatidylethanolamine ("DOPE") can be selected by ordinarily skilled artisans without undue experimentation.

Preferred embodiments of this invention involve liposomes comprising DOPE-GA, ET-18-OCH$_3$, DOPC and cholesterol ("chol"). Most preferably, presently, the liposomes comprise DOPC, chol, ET-18-O—CH$_3$ in a respective molar ratio of 4:3:1:2, wherein DOPC comprises 40 mole %, chol 30% mole, DOPE-GA 10 mole % and the etherlipid 20 mole % of the bilayer's lipid component.

The liposome can comprise an additional bioactive agent, that is, a bioactive agent in addition to the etherlipid. A "bioactive agent" is any compound or composition of matter that can be administered to animals, preferably humans. Such agents can have biological activity in animals; the agents can also be used diagnostically in the animals. Bioactive agents which may be associated with liposomes include, but are not limited to: antiviral agents such as acyclovir, zidovudine and the interferons; antibacterial agents such as aminoglycosides, cephalosporins and tetracyclines; antifungal agents such as polyene antibiotics, imidazoles and triazoles; antimetabolic agents such as folic acid, and purine and pyrimidine analogs; antineoplastic agents such as the anthracycline antibiotics and plant alkaloids; sterols such as cholesterol; carbohydrates, e.g., sugars and starches; amino acids, peptides, proteins such as cell receptor proteins, immunoglobulins, enzymes, hormones, neurotransmitters and glycoproteins; dyes; radiolabels such as radioisotopes and radioisotope-labeled compounds; radiopaque compounds; fluorescent compounds; mydriatic compounds; bronchodilators; local anesthetics; and the like.

Liposomal bioactive agent formulations can enhance the therapeutic index of the bioactive agent, for example by buffering the agent's toxicity. Liposomes can also reduce the rate at which a bioactive agent is cleared from the circulation of animals. Accordingly, liposomal formulation of bioactive agents can mean that less of the agent need be administered to achieve the desired effect. Additional bioactive agents preferred for the liposome of this invention include antimicrobial, anti-inflammatory and antineoplastic agents, or therapeutic lipids, for example, ceramides. Most preferably, the additional bioactive agent is an antineoplastic agent. Such additional bioactive agents can be loaded into liposomes by adding the agent to the lipidic solution or aqueous medium used for liposome preparation; ionizable agents can also be loaded into pre-formed liposomes using transmembrane electrochemical gradients.

The liposome of this invention can be dehydrated, stored and then reconstituted such that a substantial portion of its internal contents are retained. Liposomal dehydration generally requires use of a hydrophilic drying protectant such as a disaccharide sugar at both the inside and outside surfaces of the liposome bilayers (see U.S. Pat. No. 4,880,635). This hydrophilic compound is generally believed to prevent the rearrangement of the lipids in the liposome, so that the size and contents are maintained during the drying procedure and through subsequent rehydration. Appropriate qualities for such drying protectants are that they be strong hydrogen bond acceptors, and possess stereochemical features that preserve the intramolecular spacing of the liposome bilayer components. Alternatively, the drying protectant can be omitted if the liposome preparation is not frozen prior to dehydration, and sufficient water remains in the preparation subsequent to dehydration.

Following their preparation, liposomes are combined with a "pharmaceutically acceptable carrier," which is a medium generally acceptable for use in connection with the administration of lipids and liposomes, including liposomal bioactive agent formulations, to animals, including humans. Pharmaceutically acceptable carriers are generally formulated according to a number of factors well within the purview of the ordinarily skilled artisan to determine and account for, including without limitation: the particular liposomal bioactive agent used, its concentration, stability and intended bioavailability; the disease, disorder or condition being treated with the liposomal composition; the subject, its age, size and general condition; and the composition's intended route of administration, e.g., nasal, oral, ophthalmic, topical, transdermal, vaginal, subcutaneous, intramammary, intraperitoneal, intravenous, or intramuscular (see, for example, Nairn (1985)). Typical pharmaceutically acceptable carriers used in parenteral bioactive agent administration include, for example, D5W, an aqueous solution containing 5% weight by volume of dextrose, and physiological saline. Pharmaceutically acceptable carriers can contain additional ingredients, for example those which enhance the stability of the active ingredients included, such as preservatives and anti-oxidants.

Such pharmaceutical compositions can be used as vehicles for the administration of liposomal etherlipids to mammals in need of such treatment; these include mammals afflicted with various cancers, such as brain, breast, lung, colon or ovarian cancers, as well as leukemias, lymphomas, sarcomas and carcinomas. Liposomal etherlipids can be used to treat cancers treated with free, that is, nonliposomal, etherlipids. However, encapsulation of an etherlipid in a liposome can enhance its therapeutic index, and therefore make the liposomal etherlipid a more effective treatment.

For such treatment, an amount of a composition comprising a therapeutically effective amount of the etherlipid is administered, preferably intravenously. Therapeutically effective amounts are generally chosen in accordance with a number of factors, e.g., the age, size and general condition of the subject, the cancer being treated and the intended route of administration, and determined by a variety of means, for example, dose ranging trials, well known to, and readily practiced by, ordinarily skilled artisans given the teachings of this invention. For example, antineoplastic effective amounts of liposomal etherlipids are about the same as such amounts of free, nonliposomal, etherlipids, e.g., from about 0.1 mg of the etherlipid per kg of body weight of the mammal being treated to about 1000 mg per kg.

This invention will be better understood from the following examples. However, those of ordinary skill in the art will readily understand that these examples are merely illustrative of the invention as defined in the claims which follow thereafter.

EXAMPLES

Example 1

Preparation

Liposomes were prepared with edelfosine (ET-18-O—$CH_3$, 5 mg/ml), various other lipids obtained from Avanti Polar Lipids, Birmingham, Ala., and cholesterol (Sigma Chemical Co.). Briefly, the lipids were dissolved in an organic solvent, such as chloroform, at various mole ratios. The organic solvent was then removed, and the dried lipids were rehydrated, e.g., with Dulbecco's phosphate-buffered saline (D-PBS) (Gibco BRL Life Technologies, Grand Island, N.Y.). The resulting liposomes were extruded through 0.1 micron Nuclepore® filters (see, for example, Mayer et al., 1985). Liposome sizes were then determined by light scattering, using a Nicomp® Model 370 Submicron Particle Sizer.

Example 2

Red Blood Cell ("RBC") Hemolysis Assay

A 4% suspension of red blood cells (RBCs), 0.5 ml, was washed three times in PBS and then incubated with free (non-liposomal) etherlipid or liposomal etherlipid, prepared as described above. These samples were vortexed on a 37 deg. C. agitator for 20 hours, and were then centrifuged for 10 minutes at 3000 rpm. 0.2 ml of the resulting supernatant was diluted to 1 ml with water, and the percentage hemolysis in the sample was quantitated by spectrophotometric examination at 550 nm.

Results from these studies are presented in Table 1 (see below), wherein the concentration ($\mu$M) of edelfosine required to cause 10 % RBC hemolysis ("$HI_{10}$") in each formulation is set forth. The table's first column is a shorthand designation of the particular formulation, "ELL" standing for "etherlipid liposome." The second column indicates the components of the formulation tested, including dioleoyl phosphatidylethanolamine ("DOPE"), cholesterol ("CHOL"), dioleoylphosphatidylethanolamine-glutaric acid ("DOPE-GA"), dioeloyl phosphatidylcholine ("DOPC"), palmitoyloleoyl phosphatidylcholine ("POPC"), distearoyl phosphatidylcholine ("DSPC"), egg phosphatidylcholine ("EPC") and edelfosine ("EL," for etherlipid). The respective molar ratios of the various lipid components are also set forth. The last row of the table gives the $HI_{10}$ value for edelfosine alone, i.e., not incorporated in a liposome.

TABLE 1

| Formulation | Composition | $H_{10}$ |
|---|---|---|
| ELL 20 | DOPE:CHOL:DOPE-GA:EL 4 3 1 2 | 1726 ± 160 |
| ELL 12 | DOPC:CHOL:DOPE-GA:EL 4 3 1 2 | 670 ± 60 |
| ELL 40 | DOPC:CHOL:DOPE-GA:EL 4 3 1 2 | 65 ± 6 |
| ELL 28 | DOPC:CHOL:DOPE-GA:EL 4 3 1 2 | 32 ± 3 |
| ELL 25 | DOPC:CHOL:DOPE-GA:EL 3 3 1 3 | 537 ± 50 |
| ELL 30 | DOPC:CHOL:DOPE-GA:EL 4 3 1 2 | 314 ± 30 |
| Edelfosine | — | 5 ± 1 |

Example 3
Fluorescence Spectroscopy

Figure 1:
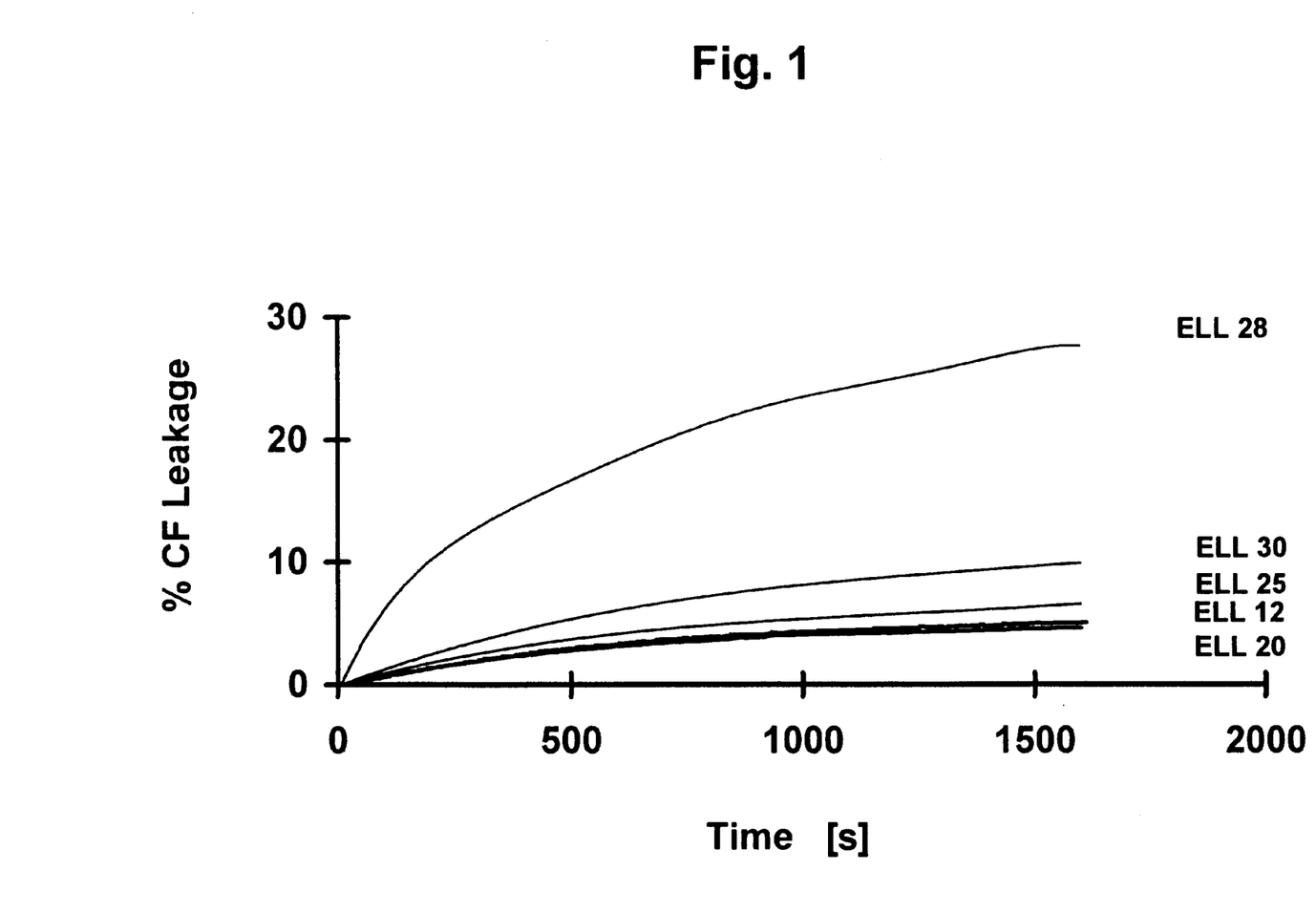

Liposomes were prepared as described above, and in the presence of an aqueous solution of 0.1 M 6-carboxyfluorescein ("CF"); free CF was then removed by gel filtration. CF efflux from liposomes over time was monitored by measuring, at 520 nm (excitation at 490 nm), increases in CF fluorescence in the aqueous phase external to the liposomes, upon their incubation in PBS at 48 deg. C. Fluorescence values, presented in FIG. 1 herein, are expressed as a percentage increase in CF fluorescence relative to the total CF fluorescence found after disrupting liposomes with Triton X-100.

Figure 2:
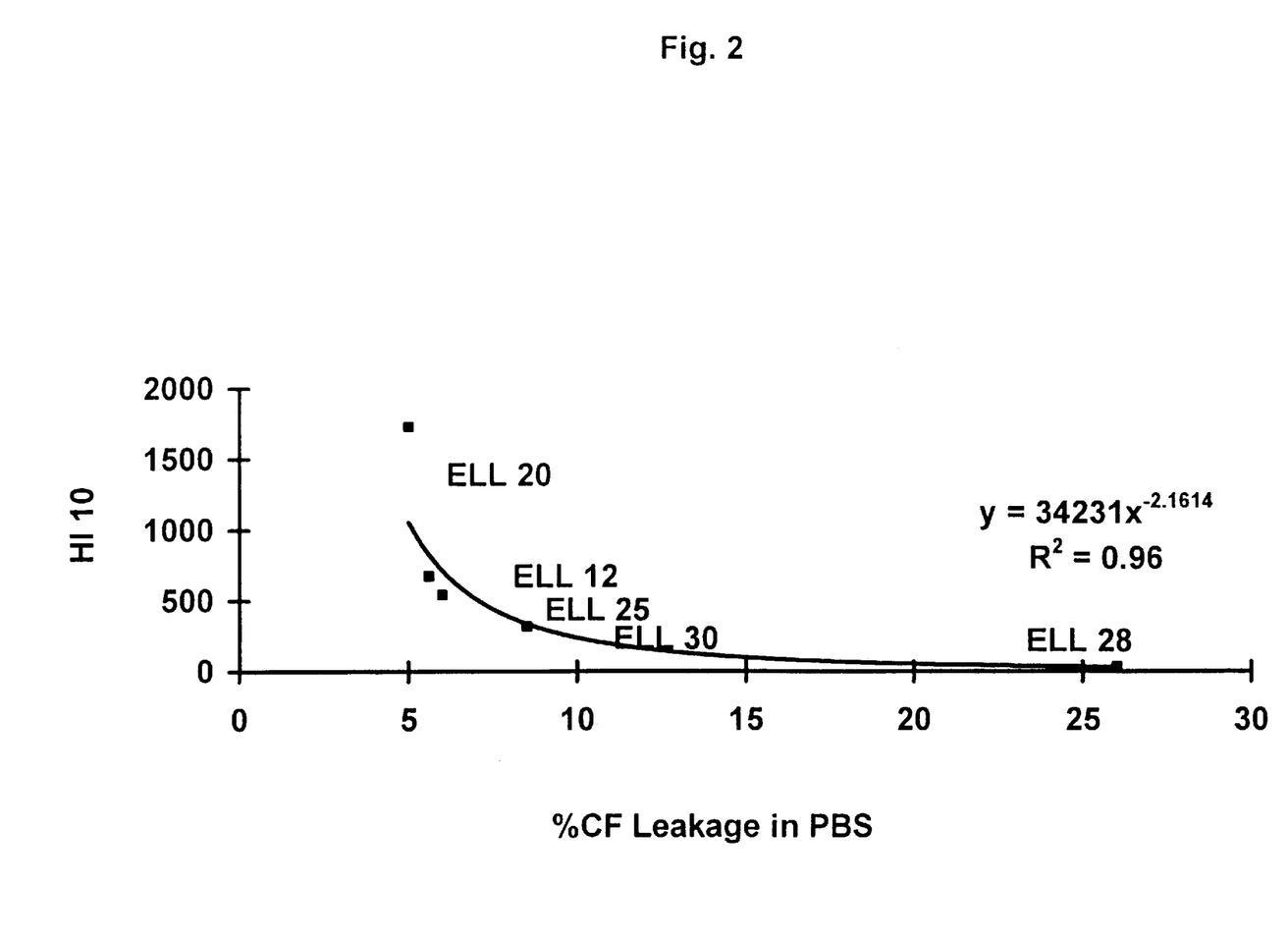
FIG. 2. Comparison of Hemolytic Activity and CF Leakage in Etherlipid Liposomes. From top-to-bottom: ELL 20-ELL 12-ELL 25-ELL 30-ELL 28 ($y=34231x^{-2.1614}$; $R^2=0.96$). Y-axis: $HI_{10}$; x-axis: % CF leakage upon incubation in PBS.
Figure 3:
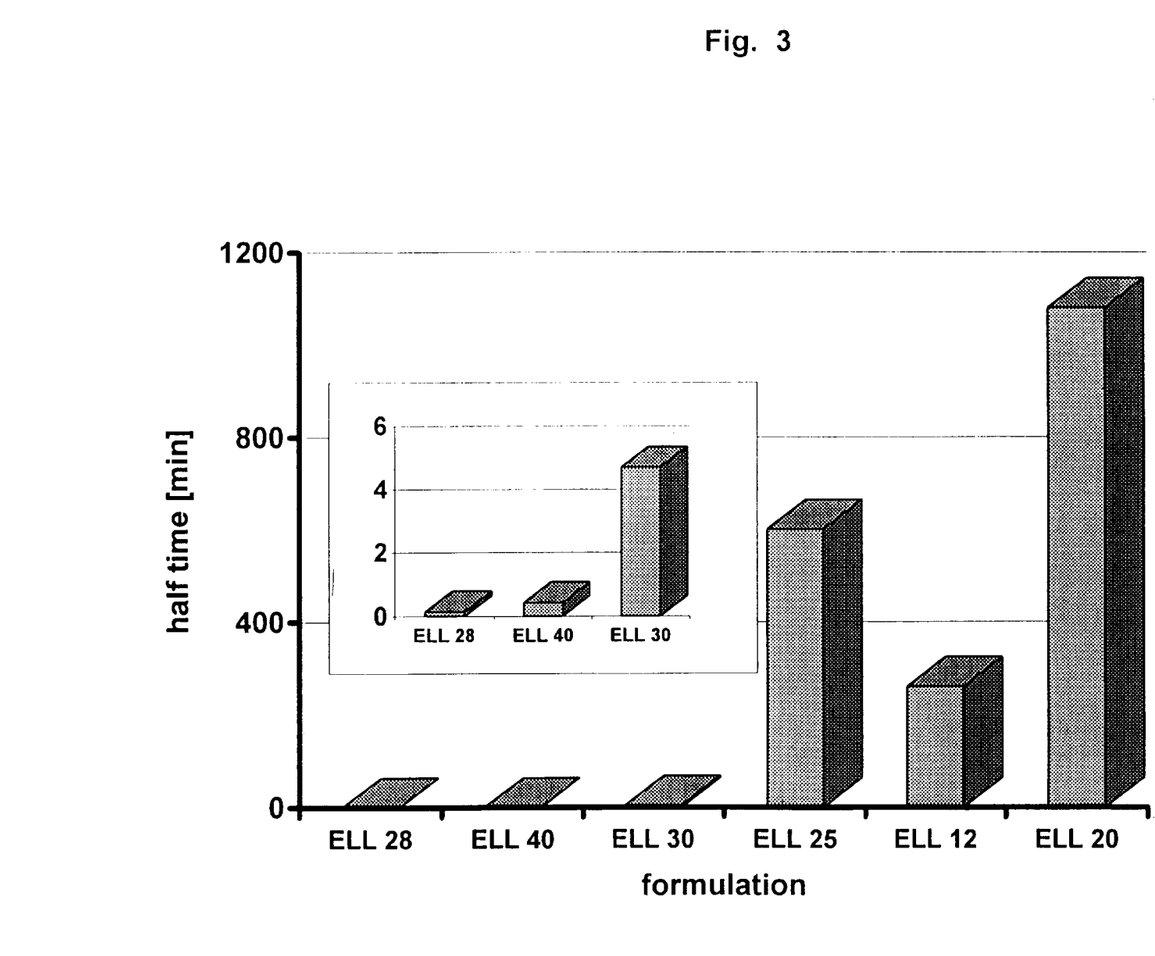
FIG. 3. Stability of Etherlipid Liposomal Formulations on Incubation in 0.5% Serum at 37 Degrees Celsius. Y-axis: time (minutes); x-axis (from left-to-right): ELL 28, ELL 40, ELL 30; ELL 25; ELL 12; ELL 20. Inset: Y-axis: time (minutes); x-axis: ELL 28, ELL 40, ELL 30.

FIG. 2 herein compares hemolytic activity and CF leakage in various liposomal formulations described in Table 1, upon incubation of the liposomes in PBS at 48 deg. C. for 25 minutes. FIG. 3 compares the time required for 50% CF leakage in various liposomal formulations, upon their incubation in 0.5% serum at 37 deg. C.

REFERENCES CITED

U.S. Patent Documents
U.S. Pat. Nos. 4,159,988, 4,163,748, 4,235,871, 4,382,035, 4,522,803, 4,588,578, 4,734,225, 4,804,789, 4,837,028, 4,920,016, 4,975,282, 5,008,050, 5,013,556, 5,030,453, 5,059,421, 5,077,056, 5,169,637, 3,752,886
Foreign Patent Documents
WO089/008846, 1,583,661, 4,132,345
Others
Bazill and Dexter, Cancer Res. 50: 7505 (1990).
Berdel, Br. J. Cancer 64: 208 (1991); Berdel, Onkologie 13: 245 (1990).
Bhatia and Hadju, Lipids 26(12): 1424 (1991).
Blume et al., Biochim. Biophys. Acta. U1149U: 180 (1993)
Darnell et al., *Molecular Cell Biology*, Scientific American Books, Inc. (1986), New York, pp. 573–575.
Deamer and Uster, "Liposome Preparation: Methods and Mechanisms," in: *Liposomes* (M. Ostro, ed.), Marcel Dekker, Inc., New York (1983), pp. 27–52.
Dietzfelbinger et al., Cancer Res. 53: 3747 91993).
Gabizon et al., Pharm. Res. 10(5): 703 91993)
Layton et al., Eur. J. Cancer 16: 64 (1980).
Lewis and McElhaney, "The Mesomorphic Phase Behavior of Lipid Bilayers," in *The Structure of Biological Membranes* (P. Yeagle, ed.), CRC Press, Inc. (1992), Boca Raton, Fla., pp. 73–155, at pp. 123–126.
Mayer et al., Biochim. Biophys. Acta 817: 193 (1985).
Muschiol et al., Lipids 22(11): 930 (1987).
Nairn, in: *Remington's Pharmaceutical Science* (A. Gennaro, ed.), Mack Publishing Co., Easton, Pa, (1985), pp. 1492–1517.
Paphadjopoulos et al., Biochem. Biophys. Acta 135: 624 (1968).
Park et al., Biochim. Biophys. Acta. 1108: 257 (1992).
Powis et al., Cancer Res. 52: 2835 (1992).
Powis et al., Cancer Res. 50: 2203 (1990).
Reed et al., Life Sci. 49: 1221 (1991).
Runge et al., JNCI. 64(6): 1301 (1980).
*Stedman's Medical Dictionary (Illustrated)* (24th edition, J. V. Basmajian et al., eds.), Williams and Wilkins, Baltimore, Md. (1982), pp. 707-708.
Tritton and Hickman, Cancer Cells 2(4): 95 (1990).
Workman, Cancer Cells 3(8): 315 (1991).
Workman et al., Biochem. Pharmacol. 41(2): 319 (1991).
Zeisig et al., anti-cancer drugs 4: 57 (1993).

What is claimed is:

1. A method of preparing a pharmaceutical composition which comprises the steps of:
   (a) preparing a liposome having a bilayer comprising a lipid component which comprises an etherlipid and a headgroup-derivatized lipid; and,
   (b) combining the liposome product of step (a) with a pharmaceutically acceptable carrier,
   wherein:
   the headgroup-derivatized lipid comprises a phosphatidylethanolamine linked at the ethanolamine group to a moiety selected from the group consisting of dicarboxylic acids and polyethylene glycols;
   the etherlipid has the formula:

$R_1$ is $Y_1Y_2$;
   $Y_2$ is $CH_3$ or $CO_2H$;
   $Y_1$ is $(CH_2)_{n1}(CH=CH)_{n2}(CH_2)_{n3}(CH=CH)_{n4}$
   $(CH_2)_{n5}(CH=CH)_{n6}(CH_2)_{n7}(CH=CH)_{n8}$
   $(CH_2)_{n9}$;
   the sum of n1+2n2+n3+2n4+n5+2n6+n7+2n8+n9 is an intefer of from 3 to 23;
   n1 is zero or an integer of from 1 to 23;
   n3 is zero or an integer of from 1 to 20;
   n5 is zero or an integer of from 1 to 17;
   n7 is zero or an integer of from 1 to 14;

n9 is zero or an integer of from 1 to 11; and, each of n2, n4, n6 and 8 is independently zero or 1;

Z is oxygen or sulfur;

$R_2$ is an alkyl group or a halogen-substituted alkyl group having the formula $(C(X_1)_{n10}(X_2)_{n11})_{n12}CX_3X_4X_5$;

each of $X_1$, $X_2$, $X_3$, $X_4$ and $X_5$ is independently H or a halogen atom;

each of n10 and n11 is independently equal to zero, 1 or 2;

n12 is zero or an integer of from 1 to 23;

when n12 is not equal to zero, the sum of n10+n11 is equal to 2; and, the headgroup-derivatized lipid comprises from about 5 mole percent to about 20 mole percent of the lipid bilayer and the etherlipid comprises from greater than about 10 mole percent to less than about 30 mole percent of the lipid bilayer.

2. The method of claim 1, wherein step (a) comprises the steps of:

(a) dissolving the lipid component in an organic solvent;

(b) removing the organic solvent from the lipid solution of step (a); and, (c) hydrating the product of step (b) with an aqueous phase so as to form liposomes.

3. The method of claim 2, further comprising the step of adding an additional bioactive agent to the organic solvent of step (a) or the aqueous phase of step (c).

4. The method of claim 2, further comprising the step of extruding the liposomes produced in step (c) through a filter so as to produce unilamellar liposomes.

5. The method of claim 4, wherein the filter has a pore size of about 100 nm.

6. The method of claim 4, further comprising the step of loading an additional bioactive agent into the liposome by way of an electrochemical potential across the liposome's bilayer.

7. The method of claim 1, wherein the headgroup derivatized lipid comprises dioleoyl phosphatidylethanolamine linked to glutaric acid.

8. The method of claim 1, wherein the etherlipid is:

9. The method of claim 1, wherein the lipid component also comprises cholesterol and dioleoyl phosphatidylcholine.

10. The method of claim 1, wherein the lipid component comprises dioleoyl phosphatidylcholine, cholesterol, dioleoyl phosphatidylethanolamine-glutaric acid and the etherlipid:

and wherein the lipid component comprises about 40 mole percent dioleoyl phosphatidylcholine, about 30 mole percent cholesterol, about 10 mole percent dioleoyl phosphatidylethanolamine-glutaric acid and about 20 mole percent of the etherlipid.

* * * * *